United States Patent
Wehrli et al.

(10) Patent No.: US 7,643,664 B2
(45) Date of Patent: *Jan. 5, 2010

(54) VIRTUAL BONE BIOPSY (VBB) SYSTEM

(75) Inventors: Felix W. Wehrli, Bala Cynwyd, PA (US); Bryon R Gomberg, San Francisco, CA (US)

(73) Assignee: The Trustees of the University of Pennsylvania, Philadelphia, PA (US)

(*) Notice: Subject to any disclaimer, the term of this patent is extended or adjusted under 35 U.S.C. 154(b) by 0 days.

This patent is subject to a terminal disclaimer.

(21) Appl. No.: 12/352,138

(22) Filed: Jan. 12, 2009

(65) Prior Publication Data

US 2009/0154786 A1 Jun. 18, 2009

Related U.S. Application Data

(63) Continuation of application No. 10/497,747, filed on Sep. 17, 2004, now Pat. No. 7,477,770.

(30) Foreign Application Priority Data

Dec. 5, 2002 (WO) .................... 02/38753

(51) Int. Cl.
  *G06K 9/00* (2006.01)
  *A61B 6/00* (2006.01)
(52) U.S. Cl. .................... 382/131; 382/275; 378/21
(58) Field of Classification Search ................ 382/100, 382/128, 129, 130, 131, 132, 133, 134, 168, 382/172, 181, 193, 203, 209, 219, 224, 232, 382/255, 260, 274, 275, 276, 305, 318, 320; 600/407, 410; 324/309; 378/4, 21, 24

See application file for complete search history.

(56) References Cited

U.S. PATENT DOCUMENTS

| | | | | |
|---|---|---|---|---|
| 4,903,202 A | * | 2/1990 | Crawford | 382/131 |
| 4,905,148 A | | 2/1990 | Crawford | 364/413 |
| 4,914,589 A | * | 4/1990 | Crawford | 382/131 |
| 5,247,934 A | | 9/1993 | Wehrli et al. | 128/653.2 |
| 5,270,651 A | | 12/1993 | Wehrli | 324/308 |
| 5,633,951 A | | 5/1997 | Moshfeghi | 382/154 |
| 5,647,360 A | | 7/1997 | Bani-Hashemi et al. | 128/653.1 |
| 5,998,997 A | | 12/1999 | Ramanathan et al. | 324/309 |
| 6,185,444 B1 | | 2/2001 | Ackerman et al. | 600/410 |
| 6,249,692 B1 | | 6/2001 | Cowin | 600/407 |
| 6,278,891 B1 | | 8/2001 | Reiderman et al. | 600/410 |
| 6,285,901 B1 | | 9/2001 | Taicher et al. | 600/410 |

(Continued)

OTHER PUBLICATIONS

Aaron, et al., "Secondary osteoporosis and the microanatomy of trabecular bone," *Clin. Rheumatology* 8(S2):84-88 (1989).

(Continued)

*Primary Examiner*—Seyed Azarian
(74) *Attorney, Agent, or Firm*—Montgomery, McCracken, Walker & Rhoads, LLP; Evelyn H. McConathy (57) ABSTRACT

The present invention comprises a system and method for analyzing trabecular bone structure. A means for scanning the trabecular bone using a magnetic resonance image (MRI) scanner generates bone image data, which is then processed including correcting, deshading and reducing noise in the image data.

17 Claims, 1 Drawing Sheet

U.S. PATENT DOCUMENTS

| | | | | |
|---|---|---|---|---|
| 6,560,476 | B1 * | 5/2003 | Pelletier et al. | 600/410 |
| 6,625,303 | B1 * | 9/2003 | Young et al. | 382/132 |
| 6,690,166 | B2 * | 2/2004 | Ni et al. | 324/309 |
| 6,775,401 | B2 * | 8/2004 | Hwang et al. | 382/131 |
| 6,975,894 | B2 * | 12/2005 | Wehrli et al. | 600/407 |
| 2002/0022779 | A1 | 2/2002 | Kose | 600/422 |
| 2002/0191823 | A1 | 12/2002 | Wehrli et al. | 382/128 |
| 2003/0057947 | A1 | 3/2003 | Ni et al. | 324/309 |
| 2004/0114789 | A1 | 6/2004 | Saha et al. | 382/128 |
| 2004/0204644 | A1 | 10/2004 | Tsougarakis et al. | 600/410 |
| 2005/0010106 | A1 | 1/2005 | Lang et al. | 600/425 |
| 2005/0031179 | A1 | 2/2005 | Wehrli et al. | 382/131 |

OTHER PUBLICATIONS

Amling, M. et al., "Architecture and distribution of cancellous bone yield vertebral fracture clues. A histomorphometric analysis of the complete spinal column from 40 autopsy specimens," *Arch. Orthop. Trauma Surg.* 115:262-269 (1996).

Ciarelli, M. et al., "Evaluation of orthogonal mechanical properties and density of human trabecular bone from the major metaphyseal regions with materials testing and computed tomography,"*J. Orthopaedic Res.* 9:674- 682 (1991).

Consensus development conference: diagnosis, prophylaxis, and treatment of osteoporosis. *Am. J. Med.* 94(6):646-650 (1993).

DeHoff, R. et al., "Experimental determination of the topological properties of three-dimensional microstructures," *J. Microscopy* 95:69-91 (1972).

Durand, E. et al., "Cancellous bone structure: analysis of high-resolution CT images with the run-length method," *J. Comput. Assist. Tomogr.* 15:133-139 (1991).

Eastell, et al., "Classification of vertebral fractures," *J. Bone Miner. Res.* 6:207-215 (1991).

Feldkamp, L. et al., "The direct examination of three-dimensional bone architecture in vitro by computed tomography," *J. Bone Mineral Res.* 4:3-11 (1989).

Garrahan, N. et al., "A new method for the two-dimensional analysis of bone structure in human iliac crest biopsies.," *J. Microscopy*, 142:341-349 (1986).

Goldstein, S. et al., "Measurement and significance of three-dimensional architecture to the mechanical integrity of trabecular bone," *Calcif. Tissue Internal'l* 53:S127-133 (1993).

Gomberg, B. et al., "Topological analysis of trabecular bone MR images," *IEEE Trans. Med. Imaging* 19(3) (2000A).

Gordon, C. et al,"In vivo assessment of trabecular bone structure at the distal radius from high-resolution computed tomography images," *Phys. Med. Biol.* 41:495-508 (1996).

Gordon, C. et al., "In vivo assessment of trabecular bone structure at the distal radius from high-resolution magnetic resonance images," *Med. Phys.* 24:585-593 (1997).

Gordon, C. et al., "Image-based assessment of spinal trabecular bone structure from high- resolution CT images," *Osteoporos Int.* 8(4):317-325 (1998).

Gordon, C. et al., "Relation between image-based assessment of distal radius trabecular structure and compressive strength," *Can. Assoc. Radiol. J.* 49:390-397 (1998).

Goulet, R. et al., "The relationship between the structural and orthogonal compressive properties of trabecular bone," *J. Biomechanics* 27:375-389 (1994).

Gudbjartsson, H. et al., "The Rician distribution of noisy MRI data," *Magnetic Resonance Med.* 34:910-914 (1995).

Hahn, M. et al., "Trabecular bone pattern factor—a new parameter for simple quantification of bone microarchitecture," *Bone* 13:327-330 (1992).

Hildebrand, T. et al., "Quantification of bone microarchitecture with the structure model index," *Computer Meth. Biomech. Biomed. Engin.* 1:15-23 (1997).

Hildebrand, T. et al., "Direct three-dimensional morphometric analysis of human cancellous bone: microstructural data from spine, femur, iliac crest, and calcaneus," *J. Bone Miner. Res.* 14(7):1167-1174 (1999).

Hodgskinson et al., "Effects of structural variation on Young's modulus of non-human cancellous bone," *Proc. Inst. Mech. Eng.*, pt. H, 204:43-52 (1990).

Hwang, S. et al., "Probability-based structural parameters from 3D NMR images as predictors of trabecular bone strength," *Med. Phys.*, 24:1255-1261 (1997).

Hwang, S. et al., "Estimating voxel volume fractions of trabecular bone on the basis of magnetic resonance images acquired in vivo," *Internat'l J. Imaging Systems and Technol.* 10:186-198 (1999).

Hwang, S. et al., "Subvoxel processing: a new method for alleviating partial volume blurring in MR images of trabecular bone," *Proc. Internat'l Resonance in Medicine*, Eight Internat'l Meeting (Internat'l Soc. Magnetic Resonance in Medicine, Denver CO), pp. 2134 (2000).

Jensen, K. et al., "A model of vertebral trabecular bone architecture and its mechanical properties," *Bone* 11:417-423 (1990).

Kinney, J. et al., "The relationship between three-dimensional connectivity and the elastic properties of trabecular bone," *J. Bone Mineral Res.* 13:839-845 (1998).

Kleerekoper, M. et al., "The role of three-dimensional trabecular microstructure in the pathogenesis of vertebral compression fractures," *Calcif. Tissue Int.* 37:594-597 (1985).

Kong, T. et al., "Digital Topology: Introduction and Survey," *Computer Vision Graphics and Image Processing* 48:357-393 (1989).

Laib, A. et al., "Ridge number density: a new parameter for in vivo bone structure analysis," *Bone* 21(6):541-546 (1997).

Laib, A. et al., "In vivo high resolution 3D-QCT of the human forearm," *Tech. Health Care* 6(5-6):329-337 (1998).

Lane, N. et al., "Early estrogen replacement therapy reverses the rapid loss of trabecular bone volume and prevents further deterioration of connectivity in the rat," *J. Bone Miner. Res.* 14(2):206-214 (1999).

Legrand, E. et al., "Trabecular bone microarchitecture, bone mineral density and vertebral fractures in male osteoporosis," *J. Bone Miner. Res.* 15:13-19 (2000).

Link, T. et al., "In vivo high resolution MRI of the calcaneus: differences in trabecular structure in osteoporosis patients," *J. Bone Miner. Res.* 13(7):1175-1182 (1998).

Ma, J. et al., "Fast 3D large-angle spin-echo imaging (3D Flase)," *Magnetic Resonance Med.* 35:903-910 (1996).

Majumdar, S. et al., "Correlation of trabecular bone structure with age, bone, mineral density, and osteoporotic status: in vivo studies in the distal radius using high-resolution magnetic resonance imaging," *J. Bone Mineral Res.* 12:111-118 (1997).

Majumdar, S. et al., "High-resolution magnetic resonance imaging: three-dimensional trabecular bone architecture and biomechanical properties," *Bone* 22(5):445-454 (1998).

Morita, M. et al., "Progression of osteoporosis in cancellous bone depending on trabecular structure," *Ann. Biomed. Eng.* 22:532-539 (1994).

Mosekilde, L. "Age-related changes in vertebral trabecular bone architecture—assessed by a new method," *Bone* 9:247-250 (1988).

Mosekilde, L. "Consequences of the remodelling process for vertebral trabecular bone structure: a scanning electron microscopy study (uncoupling of unloaded structures)," *Bone Mineral* 10(1):13-35 (1990).

Muller, R. et al., "Noninvasive bone biopsy: A new method to analyze and display the three-dimensional structure of trabecular bone," *Phys. Med. Biol.* 39:145-164 (1994).

Muller, R. et al.,"In vivo reproducibility of three-dimensional structural properties of noninvasive bone biopsies using 3D-pQCT," *J. Bone Mineral Res.* 11:1745-1750 (1996).

Nelson, D. et al., "What is a Vertebral Fracture?" In: Marcus R, Feldman D, Kelsey J (eds.) *Osteoporosis*, Academic Press, San Diego, pp. 613-621 (1996).

Oden, Z. et al., "The effect of trabecular structure on DXA-based predictions of bovine bone failure," *Calcif. Tissue Int*, 63:67-73 (1998).

Odgaard, A. et al., "Quantification of connectivity in cancellous bone, with special emphasis on 3-D reconstructions," *Bone* 14:173-182 (1993).

Odgaard, A. et al., "Fabric and elastic principal directions of cancellous bone are closely related," *J. Biomechan.* 30:487-495 (1997).

O'Neill, T. et al., "Definition and diagnosis of vertebral fracture," *J. Rheumatol.* 24(6):1208-1211 (1997).

Parfitt, A. "Stereologic Basis of Bone Histomorphometry: Theory of Quantitative Microscopy and Reconstruction of the Third Dimension," in *Bone Histomorphometry: Techniques and Interpretation*, R. R. Recker, Ed., Boca Raton, FL: CRC Press, 1981, pp. 53-87.

Parfitt, A. et al.,"Relationships between surface, volume, and thickness of iliac trabecular bone in aging and in osteoporosis. Implications for the microanatomic and cellular mechanisms of bone loss," *J. Clin. Invest.* 72:1396-1409 (1983).

Parfitt, A. "Implications of architecture for the pathogenesis and prevention of vertebral fracture," *Bone* 13:S41-47 (1992).

Peyrin, F. et al., "Micro-CT examinations of trabecular bone samples at different resolutions: 14, 7 and 2 micron level," *Technol. & Health Care* 6:391-401 (1998).

Pothuad, L. et al., "A new method for three dimensional skeleton graph analysis of porous media: application to trabecular bone microarchitecture," *J. Microsc.* 199:149-161 (2000).

Recker, R. "Architecture and vertebral fracture," *Calcif. Tissue Int.* 53 Suppl 1:S139-142 (1993).

Rosenfeld, A. "Adjacency in Digital Pictures," *Information and Control* 26:24-33 (1974).

Saha, P. et al., "3D digital topology under binary transformation with applications," *Computer Vision and Image Understanding* 63:418-429 (1996).

Saha, P. et al., "A new shape preserving parallel thinning algorithm for 3D digital images," *Pattern Recognition* 30:1939-1955 (1997).

Saha, P. et al., "Strongly normal sets of convex polygons or polyhedra," *Pattern Recognition Lett.* 19:1119-1124 (1998).

Saha, P. et al., "Determining simplicity and computing topological change in strongly normals partial tilings of $R^2$ and $R^3$," *Pattern Recognition* 33:105-118 (2000A).

Saha, P. et al., "Three-dimensional digital topological characterization of cancellous bone architecture," Internal'l *J. Imaging Systems and Technology*, 11:81-90 (2000B).

Shrout, P. et al., "Intraclass correlations: Uses in assessing rater reliability," *Psychological Bull.* 86:420-428 (1979).

Siffert, R. et al., "Dynamic relationships of trabecular bone density, architecture, and strength in a computational model of osteopenia," *Bone* 18:197-206 (1996).

Song, H. et al.,"In vivo micro-imaging using alternating navigator echoes with applications to cancellous bone structural analysis," *Magnetic Resonance Med.* 41:947-953 (1999).

Steiner, E. et al., "Radiology of Osteoporosis," in: Marcus R, Feldman D, Kelsey J (eds.) *Osteoporosis*, Academic Press, San Diego, pp. 1019-1050 (1996).

Udupa, J. et al., "Boundary and object labelling in three-dimensional images," *Computer Vision Graphics and Image Processing* 51:355-369 (1990).

Vesterby, A. "Star volume of marrow space and trabeculae in iliac crest: sampling procedure and correlation to star volume of first lumbar vertebra," *Bone* 11:149-155 (1990).

Vesterby, A. et al., "Biologically meaningful determinants of the in vitro strength of lumbar vertebrae," *Bone* 12:219-224 (1989).

Wehrli, F. et al., "Cancellous bone volume and structure in the forearm: noninvasive assessment with MR microimaging and image processing [published erratum appears in *Radiology* Jun. 1998; 207(3):833]," *Radiology* 206:347-357 (1998B).

Wehrli, F. et al., "New architectural parameters derived from micro-MRI for the prediction of trabecular bone strength," *Technique Health Care* 6:307-320 (1998A).

Wehrli, F. et al., "Cross-sectional study of osteopenia by quantitative magnetic resonance and bone densitometry," *Radiology* 217:527-538 (2000).

Wehrli, F. et al., "Digital topological analysis of in vivo MR microimages of trabecular bone reveals structural implications of osteoporosis," *J. Bone Mineral Research*, 16:8, 1520-1531 (2001).

Wessels, M. et al., "Connectivity in human cancellous bone by three-dimensional magnetic resonance imaging," *Medical Physics* 24:1409-1420 (1997).

Wu, Z. et al., "A Bayesian approach to subvoxel tissue classification in NMR microscopic images of trabecular bone," *Magnetic Resonance Med.* 31:302-308 (1994).

\* cited by examiner

FIG. 1

VIRTUAL BONE BIOPSY (VBB) SYSTEM

CROSS REFERENCE TO RELATED APPLICATIONS

This application is a Continuation of U.S. patent application Ser. No. 10/497,747, filed Sep. 17, 2004, issued as U.S. Pat. No. 7,477,770, which claims priority to U.S. Provisional Application No. 60/336,985, filed Dec. 5, 2002, which is incorporated herein in its entirety. This application is also related to U.S. Continuation-in-Part application Ser. No. 10/121,470, filed Apr. 11, 2002, which was a U.S. Continuation-in-Part application Ser. No. 09/820,225, filed Mar. 28, 2002.

GOVERNMENT INTEREST

This invention was supported in part by Grant No. RO1 AR049553 from the National Institutes of Health. Accordingly, the Government may have certain rights in this invention.

BACKGROUND

The present invention relates generally to bone structure analysis. More specifically, the present invention relates to a method of analyzing bone structure using magnetic resonance micro imaging ($\mu$-MRI).

Bone is a composite biomaterial designed to provide high static and impact strength. Its inorganic fraction is made up of calcium apatite bound to the osteoid, which consists primarily of type-I collagen. Bone constantly remodels, a term used to indicate a dynamic equilibrium that exists between formation and resorbtion. New bone is deposited by osteoblasts, the bone-forming cells, while old bone is resorbed by osteoclasts, the bone-resorbing cells. Although incompletely understood, bone remodeling allows the structure to adapt to the forces to which it is subjected, but also serves as a mechanism to repair fatigue damage. In the adult skeleton, after cessation of growth, an equal amount of bone is resorbed as new bone is formed, i.e. there is no net bone balance. Bone formation and resorbtion are tightly coupled processes involving a complex interplay of various hormones. This regulation acts in concert with mechanical stimuli mediated by osteocytes, a third type of cell embedded in the bone matrix, that act as pressure transducers activating osteoblasts to induce new bone formation.

The architecture and geometry of bone is determined by its anatomic location and function. The long bones (extremities) consist mainly of cortical (compact) bone. For example, in the center of the femur, i.e. between the two joints, the bone has the shape of a hollow tube with a wall thickness of several millimeters. By contrast, near the joints of long bones and in the axial skeleton (trunk, vertebrae) bone is predominantly of the trabecular kind, consisting of a network of interconnected struts and plates fused to a surrounding relatively thin cortical shell. It is believed that this design of nature ensures optimum strength at minimum weight.

Osteoporosis (process causing "porous" bone) is a multifactorial disease leading to bone loss and architectural deterioration (see, for example, Parfitt, *Bone* 13:S41-47, 1992.). Whereas uniform thinning would clearly impair the trabecular network's strength, the implication of loss of connectivity through disruption of struts and plates has much more severe consequences. It has been shown, for example, that in the vertebrae, horizontal connecting trabeculae are lost preferentially during pathogenesis of osteoporosis (Mosekilde, *Bone and Mineral*, 10:13-35, 1990), causing the bone to fail by buckling. It is thus clear that through depletion of bone mass at critical locations in the network, loss of a small amount of bone mass can have disproportionately large mechanical consequences.

A number of laboratory studies provide compelling evidence for the contributions of trabecular architecture to the stiffness and ultimate strength of trabecular bone. A meta-analysis of 38 studies suggests that on the average about 60% of the bone's mechanical competence can be explained by variations in the apparent density (bone mass/tissue volume) alone (see, Turner, et al., *J Biomechanics*, 23:549-561, 1990 and Turner, et al., *J Biomechanics*, 25:1-9, 1992) found that density and measures of fabric (a measure of structural anisotropy) could explain up to 90% of the variance in trabecular bone's elastic constants. There is equally strong support from clinical studies for the role of architecture in conferring strength to trabecular bone (Kleerekoper, et al., *Calcified Tissue International*, 37:594-597, 1985) and (Legrand, et al., *J. Bone Mineral Research*, 15:13-19, 2000).

Most studies investigating trabecular bone architecture are based on cadaveric material or bone biopsies. The latter are typically performed at the iliac crest in the form of a cylindrical core of bone tissue being removed with a trephine (see, for example, Chavassieux, et al., *Osteoporosis*, 2:501-509, 2001). The specimen then is embedded in methylmethacrylate, stained and sectioned. Subsequently, the stained sections are examined by microphotography and histomorphometric parameters derived with the aid of an image analysis system. This approach, besides its invasiveness that precludes serial repeat studies in patients, is two-dimensional, although stereologic approaches enable, to a limited extent, the derivation of the third dimension (Gundersen, et al., *Archives of Physical Medicine in Surgery*, 96:379-394, 1988) and (Parfitt, *Bone Histomorphometry: Techniques and Interpretation*, Recker, Ed. Boca Raton, Fla.: CRC Press, 53-87, 1981.) More recently, bone biopsies have been imaged by micro computed tomography ($\mu$-CT) and 3D structural measures derived from such images (see, for example, Hildebrand, et al., *J Bone Miner. Res.*, 14:1167-74, 1999.) thus alleviating one of the limitations of this approach.

Accordingly, there is a need for a method of analyzing bone structure that overcomes all of the limitations of the current methods.

SUMMARY

The present invention comprises a system and method for analyzing trabecular bone structure. A means for scanning the trabecular bone using a magnetic resonance image (MRI) scanner generates bone image data, which is then processed including correcting, deshaping and reducing noise in the image data.

Additional objects, advantages and novel features of the invention will be set forth in part in the description, examples and figures which follow, all of which are intended to be for illustrative purposes only, and not intended in any way to limit the invention, and in part will be come apparent to those skilled in the art on the examination of the following, or may be learned by practice of the invention.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

DESCRIPTION OF PREFERRED EMBODIMENT(S)

The mechanical competence of trabecular bone, the type of bone constituting the vertebrae and ends of the long bones, is largely determined by the bone's volume fraction and architectural make-up. Experimental and clinical evidence suggests that up to 50% of trabecular bone strength is determined by parameters characterizing the network's architecture. Although rarely clinically indicated because of its invasiveness, a bone biopsy can provide detailed insight into the bone's structural arrangement. Advances in magnetic resonance micro-imaging (µ-MRI), in conjunction with new image processing and feature extraction approaches, now allow detailed structural information to be obtained by what is preferably referred to as "virtual bone biopsy" (VBB). A VBB data acquisition and analysis system and method acquires magnetic resonance (MR) microimages of trabecular bone and produces measures for trabecular network properties to assist in the evaluation of bone diseases, such as osteoporosis and renal osteodystrophy.

Figure 1:
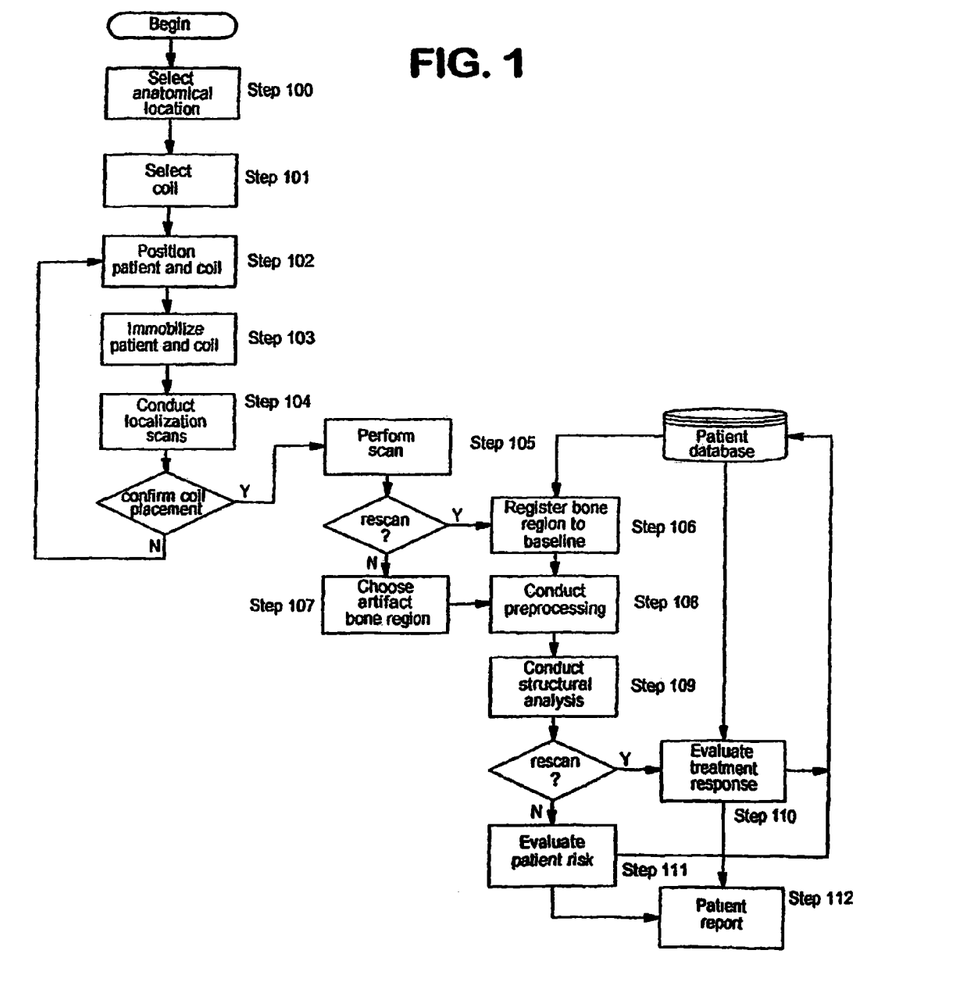
FIG. 1 is a flow diagram of the method of analyzing bone structure in accordance with a preferred embodiment of the present invention.

The VBB system is divided into three components: acquisition hardware, acquisition software and a processing system. The acquisition hardware comprises the dedicated MR coils that act as near field antennas to detect the magnetic precession of hydrogen atom nuclei. The first component of the acquisition software comprises the pulse sequence that produces the detected transverse magnetization, it performs high-speed data acquisition, and incorporates navigator signals (echoes) used for motion correction. The second component to the acquisition software is the interactive data language (IDL) program that interprets the raw data from the scanner, analyzes the k-space for subject motion, thus yielding a motion corrected reconstruction of the MR image data. The processing system comprises a series of routines that when applied sequentially will analyze the acquired data, and produce results used for evaluation of trabecular bone architecture. The flow diagram of a preferred embodiment of the method of analyzing the bone structure of a patient using the VBB system is illustrated in FIG. 1.

As indicated above, the VBB, in accordance with a preferred embodiment, utilizes µ-MRI for generating the image for use in the analyzing of bone structure in a given subject. In MRI the source of contrast between bone and marrow is the strong signal from marrow contrasting against the background signal of bone. Although bone has about 15% relatively mobile water (mostly interstitial and collagen-bound), its transverse relaxation time of well below 1 millisecond precludes direct imaging of bone except with such techniques as constant-time imaging and its derivatives. For all practical purposes one may, therefore, regard bone as 'invisible' by spin-echo or gradient-echo imaging pulse sequences.

Bone marrow is either hematopoietic or fatty, thus possessing the usual properties of water or fatty acid triglyceride protons characteristic of other soft tissues. It therefore provides an almost ideal signal source for trabecular bone MRI. Unless the marrow is mixed, a binary tomographic system of only two signal components (i.e. background and marrow) is used. Mixed marrow constitutes more of a problem since the relaxation characteristics are rather different for the two marrow constituents ($T_1$~0.3 and 1 second in fatty and hematopoietic marrow, respectively) although their proton densities are nearly identical. This will lead to significantly attenuated signal for the latter unless the scans are conducted under fully relaxed conditions. Marrow at the distal end of the extremities (sites suitable for high-resolution imaging of trabecular architecture) is entirely fatty. Thus, in addition to its noninvasiveness, MRI is ideally suited for trabecular bone imaging. Its only practical limitation is SNR, which is ultimately constrained by scan time. Accordingly, the anatomic location (e.g., distal radius, distal tibia, calcaneus or other location suited for obtaining high-resolution images of trabecular structure) for analysis must be selected such that the use of MRI is not limited (Step 100). Preferably, multiple sites can be acquired in an interleaved fashion using specialized coil arrays and pulse sequences.

The coil(s) utilized for the MRI may differ depending on the anatomical location to be imaged. Accordingly, it is preferable that the selection of the appropriate coil be made after the anatomical location has been selected (Step 101). In the case of the distal radius, a preferred coil is the elliptical clamshell birdcage volume coil, which is ideal for cylindrical anatomical structures. For other anatomical locations, it is preferable to use a multiple element surface coil, such as a two-element surface coil for use on the ankle. For multiple element surface coils, the number of elements may be as high as can be supported on a given scanner system, preferably as high as eight (8) elements. The coil size or sensitive volume is preferably designed to be minimal so as to reduce sample noise, but at the same time large enough such that a sufficient volume of trabecular bone is covered at high enough signal to noise ratio (SNR) for structural analysis. In some cases, such as the distal tibia, it is preferable to design the coil to purposely collect only half the cross sectional volume so as to reduce the sample noise.

A preferred embodiment of the present invention next requires that the patient and coil be positioned (Step 102) and the anatomic region immobilized (Step 103). Patient positioning is preferably done such that it avoids patient discomfort during scanning, thus avoiding patient induced motion. External landmarks are preferably at each anatomical site to position the coil relative to the positioned anatomy. Immobilization is needed to avoid gross motion of the anatomical region and must allow for adequate comfort while maintaining the anatomy and coil fixed relative to the magnet center. It is preferable that the immobilization means include a temporary or permanent cast, using air-evacuated plastic bags, or using an active vacuum system. Although the immobilization means disclosed is preferable, any immobilization means may be utilized.

Once the anatomical region and the coil have been immobilized, an imaging pulse sequence must be selected and optimized for localization of internal anatomical landmarks, such as growth plate, cortical endplate and the like. (Step 104) Optimization includes the selection of pulse sequence for maximum contrast of bone landmarks, and resolution to allow accurate localization of the microimaging scan relative to this anatomy. Typically the localization scan involves an initial axial localizer to determine the location of the bone, and then a sagittal or coronal high-resolution localizer, for evaluation of coil positioning and localization of the microimaging volume (i.e., the coil). The high-resolution localizer is acquired with the frequency encoding direction parallel to the anatomical axis, such that the maximum resolution is available for the microimaging volume placement. The preferred pulse sequence is the FLASE pulse sequence, those having skill in the art know that other pulse sequences may be utilized as well, such as a conventional 2D or 3D spin-echo pulse sequence, a gradient-echo pulse sequence, pulse sequences that rely on projection reconstruction or spiral scanning of k-space.

A determination is then made, based on the localization scans, as to whether the coil is properly placed in relation to the anatomical region. If the coil is misplaced as determined by the signal intensity over the anatomical region, Steps 102-104 are repeated. Coil misplacement can be measured from the sensitivity region on the scanner relative to the internal landmarks to determine the exact misplacement distance, thus allowing single repeat alignment and avoiding time consuming iterative realignments.

Upon confirmation of the proper alignment of the coil, the anatomical region is scanned. (Step 105). It is preferable that images be acquired at the highest possible resolution so as to allow reconstruction of the 3D architecture after further processing of the data. Accordingly, pulse sequences are preferably used that optimize the acquisition of signals from the marrow region of the trabecular bone scanned. The resolution and SNR need to be adjusted so that the resolution is capable of capturing the 3D structure of the bone in both the longitudinal and transverse directions, while maintaining sufficient SNR for accurate image processing.

For repeat scans, the data collected from the VBB scan of the bone region is registered to base line study (in the case of longitudinal studies) or masking of trabecular region (baseline or single scan study). (Step 106). Registration is typically accomplished by a series of rotations and translations (rigid-body registration) or in addition elastic deformations, with the objective to precisely align baseline and repeat scans to maximize coincidence of the analysis volumes.

For those scans that are repeat scans, an artifact free portion of the scanned bone is selected for further pre-processing. (Step 107) Artifacts refer to image features that have no anatomic counterpart and may be the result of residual motion or imperfections in the imaging hardware. Artifacts are identified visually and excluded from the analysis by masking corrupted regions in the images.

The image data generated in either Step 106 or 107 is then preprocessed. (Step 108). In vivo imaging at microscopic dimensions poses unique challenges as far as prevention of and compensation for motion is concerned. Since the scan takes approximately 10-15 minutes to complete, involuntary subject motion is almost impossible to prevent even using limb restraining techniques. The problem is exacerbated by the very small pixel size on the order of 100-150 µm. Studies have shown that motion on the order of one pixel can cause sufficient blurring to corrupt the derived structural parameters to the extent that small effects (as expected, for example in response to treatment) can be masked by the effects of displacement during the scan. Restraining the anatomical location alleviates such undesired effects but may not be sufficient.

Among the approaches for motion correction, the navigator technique and autofocusing have been found to substantially reduce blurring from random displacements occurring during the scan and improving data accuracy. The navigator correction technique is widely used in many motion-sensitive applications. The underlying idea is to append additional echoes whose function is to sense small displacements that occur during the scan, to the imaging pulse sequence. After Fourier transformation these echoes result in projections along the direction of the navigator gradient.

Incorporation of gradient navigator echoes into the FLASE pulse sequence along the readout and phase-encoding axes thus allow sensing of translational displacements in x- and y-directions. From the measured displacements, a phase shift can then be computed to correct the k-space data.

Another approach to motion correction is entirely retrospective and thus obviates collection of any additional data. The technique, referred to as "autofocusing", is an iterative process that involves applying trial phase shifts to a small part of the data space (e.g., a few $k_y$ lines of data) to compensate for possible translational motion and comparing the resulting image with the original. A "focus" parameter then provides a criterion to either accept or reject the image resulting from substitution of that particular portion of k-space. A range of phase shifts is tried and the value that gives the best focus parameter value is retained. This process is then repeated by applying trial shifts to other parts of the data set. (see, Atkinson, et al., *IEEE Trans. Med. Imag.*, 16:903-910, 1997). A frequently used focus criterion is entropy, the notion being that decreased blurring lowers image entropy, but other focus criteria have been used as well. (Shannon, *Bell. Syst. Tech. J*, 27:623-656, 1948). Although, exemplary methods of correcting for motion have been disclosed, it should be noted that any method for correcting for motion can also be applied to the preprocessing of the bone image data.

Another step in the preprocessing of the bone data is deshading the image data to minimize the effects of RF inhomogeneity. At high resolution (i.e. at a voxel size much smaller than trabecular thickness) and high SNR, segmentation of the image into bone and bone marrow is straightforward. In this case the intensity histogram is bimodal and the images are binarized by setting the segmentation threshold at the midpoint of the intensity maxima for marrow and bone. However, the voxel size achievable in vivo at SNR~8-10 is usually on the order of or greater than trabecular thickness. Under these conditions the histogram coalesces into a single peak and the images can no longer be binarized since the majority of "bone" voxels contain a significant fraction of marrow. There exist various approaches to deal with this problem. An exemplary method disclosed in U.S. patent application Ser. No. 09/820,225, (the '225 application) which is herein incorporated by reference in its entirety, generates grayscale images in which pixel intensity represents the fractional occupancy of bone, i.e., a bone volume fraction (BVF) image that is free of noise and intensity anomalies as they arise from spatial variations in the received signal. Such an approach obviates the need for threshold setting and has the advantage that the full information is retained (rather than resulting in the data reduction inherent to all thresholding techniques).

The basis of this exemplary method is to iteratively deconvolve the actual histogram, which is achieved by resorting to a model histogram consisting of two δ-functions (for bone and bone marrow, respectively) as a starting point. The model histogram is first convolved with Rician noise (the type of noise inherent to modulus MR images), compared with the experimental histogram, and the error between the two histograms determined. Subsequently, the error is subtracted from the initial estimate and the process repeated until the error has fallen below a predetermined threshold. Finally, the histogram intensities are assigned to the image pixels on the basis of the probability of a pixel to contain bone and connectivity arguments. It should be noted that the above disclosed method of deshading the image data is for exemplary purposes only and should not be used to limit the present invention. Other methods of deshading the image data may be utilized in accordance with a preferred embodiment of the present invention.

While returning correct values of bone volume fraction, the noise-deconvolved images still suffer from partial volume blurring and cannot not be segmented into bone and bone marrow. Although structure analysis methods exist that effectively use as input grayscale images, analysis of network topology, requires a skeleton representation of the images. "Subvoxel processing," as disclosed, for example, in the '225 application, substantially alleviates partial volume blurring. The method rests on two simple premises: (i) smaller voxels are more likely to have high BVF and (ii) bone is contiguous, i.e., there exist no disconnected islands. The algorithm's starting point is partitioning of each voxel into eight subvoxels. In addition, it enforces strict conservation of bone mass, i.e., the total BVF in the original voxel is merely redistributed among the subvoxels. The precise amount allotted to a subvoxel is determined by the amount and location of bone outside the voxel but adjacent to the subvoxel. Thus, bone tends to be sequestered in subvoxels that are closer to other bone locations.

Noise reduction is a third preprocessing step that preferably occurs in the preprocessing of the bone image data. Since noise is not spatially correlated, it is possible to remove the image noise by looking at the spatial distribution of the noise, preferably through the histogram deconvolution method discussed above. Other methods of looking at the spatial distribution of noise in the bone image data may be utilized. Also, other methods of reducing noise in the bone image data may be utilized.

After the preprocessing of the bone image data, trabecular bone structure analysis and quantification (strength) is conducted. (Step 109). Trabecular bone structure analysis comprises topological analysis, structural anisotropy and structural thickness, for example. The etiology of bone loss in the most common form of osteoporosis involves fenestration of trabecular plates with eventual progression to rods and disconnection of rod-like trabecular elements.

An exemplary method of conducting topological analysis is disclosed in U.S. patent application Ser. No. 10/121,470, which is incorporated herein by reference. Topological classification requires skeletonized images (skeletonization reduces an object to a union of surfaces and curves, preserving its topology and the core shape) and relies on the numbers of three local topological entities—objects, tunnels (e.g., the loop in a doughnut or the handle of a coffee mug), and cavities (e.g., the interior of a hollow ball). The method works on an object S that can be expressed as a union of finitely many surfaces and curves. After a point p is removed from a surface in S (e.g., a puncture on a surface), in a sufficiently small neighborhood of p, S forms a tunnel or loop. Conversely, if p lies on a curve in S, the same operation breaks S in a small neighborhood of p. It generates multiple tunnels if p lies on a junction of surfaces, or a tunnel and multiple components if it is on a junction of a surface and one or more curves. In extending this principle to digital space as it applies to the current application, the following steps are required: (1) binarization of a bone volume fraction image, thereby obtaining a set of trabecular bone voxels and a set of marrow voxels, (2) computation of the skeleton of the binarized trabecular bone network, (3) computation of topological entities, preferably, the number of tunnels and cavities in a 3×3×3 neighborhood, and (4) non idealized situations in digital space, e.g., removal of a point at the junction of curves may lead to the formation of a tunnel in the 3×3×3 neighborhood in digital space.

In a preferred embodiment binarization is executed at a fixed threshold pre-computed from a training set yielding the minimum structural change. The skeletonization method, disclosed in Saha et. al., *Pattern Recognition,* 30:1939-1955, 1997 is utilized in a preferred embodiment, since it is robust under noise and rotation. However, other methods of binarization may also be utilized. An efficient method to compute the numbers of objects, tunnels, and cavities in the 3×3×3 neighborhood of a point after its removal (i.e., the point is considered as marrow for computation purpose) is disclosed in U.S. patent application Ser. No. 10/121,470.

To resolve the situation of non-ideal situations in the digital case, the entire classification process is completed in three sequential steps, which uses two decision tables in two steps—the first provides a partial classification, while the latter gives a final classification. Some corrections and assignments of profile classes are performed in the final step. Accordingly, the trabecular bone voxels are classified into I (isolated)-, C (curve)-, CE (curve edge)-, S (surface)-, SE (surface edge)-, CC (curve-curve junction)-, SC (surface-curve junction)-, SS (surface-surface), PI (profile interior)-, and PE (profile edge)-classes.

Age-related and postmenopausal bone loss proceeds via a non-homogeneous thinning of trabecular plates, leading to fenestration of the plates and their conversion to struts, which may become disconnected and eventually entirely resorbed. The process therefore manifests itself in a reduction in topological surface density and concomitant increase in the density of curve voxels. The consequence of these structure conversions is amplified by computing a surface-to-curve ratio (S/C), which is the ratio of the sum of all surface-type voxels (S, SE, SS, SC) divided by the sum of all curve-type voxels (C, CE, CC). This ratio is thus expected to be a sensitive indicator for the conversion of plates to rods. Similarly, an erosion index has been defined as the ratio of the sum of parameters that are expected to increase upon osteoclastic resorption (e.g., CE and SE-types), divided by the sum of parameters that are expected to decrease (e.g. S-type). Perforation of plates, for example, decreases the number of surface-interior voxels. Likewise, disruption of rods decreases the number of curve-interior (C-type) voxels while increasing the number of curve-edge (CE-type) voxels.

Nevertheless, the above disclosed methods of topological analysis are for exemplary purposes and should not be used to limit the present invention. As those skilled in the art would recognize, other methods of topological analysis are known and can be used in accordance with the present invention.

Trabecular bone is inherently structurally anisotropic, i.e., the trabeculae have, at most locations in the skeleton, a preferred direction. Structural orientation (also denoted 'fabric') is a consequence of Wolff's Law, which states that bone remodels in response to the stresses to which is subjected. Skeletonization converts plates to surfaces and rods to curves, thus local structural orientation information can be obtained by measuring the orientation of these curves and surfaces. By isolating a specific topological structure type, such as surfaces, and determining the local orientation of the trabecular network at that location by fitting an analogous analytical structure, in this case a plane, the structural anisotropy can be evaluated.

Combining the results of these local orientations to evaluate global or regional anisotropy is done by analysis of the histogram of orientations for the selected region. For large regions these distributions represent overall preferential directions of the trabecular network, with their distributions following the complex biomechanical loads as predicted by Wolff's law. When the region for structural analysis is small enough, the polar and azimuthal components of these distributions are typically bell shaped, leading to characterization by a Gaussian distribution. By fitting these component distributions to Gaussian curves, the structural anisotropy can be completely described by the peak location (preferred orientation), Gaussian width, Gaussian height, and baseline height. Analysis of the orientation of surface edges or surface-surface junctions can be done analogously to the orientation of curves. However, the above disclosed methods of determining structural anisotropy are for exemplary purposes, and should not be used to limit the present invention. As those skilled in the art know, other methods of determining structural anisotropy are known (e.g., image gradient analysis and tensor scale analysis) and can be used in accordance with the present invention.

Topology per se cannot predict a network's strength since it carries no information on the nature of the connections. However, along with information on the scale of the network such as the thickness of trabecular elements, topology is a likely determinant of the structure's mechanical competence. A relatively intact network of very thin trabeculae would be inferior to one with the same topological make-up consisting of thicker trabeculae. It is known, for example, that certain pathological processes such as the action of supraphysiologic levels of corticosteroid, primarily lead to homogeneous thinning and during the early phase of atrophy would not significantly reduce the number of connections. The bone in steroid-treated subjects is compromised as evidenced by their increased fracture rates. Conversely, recovery is more likely to restore the reduced mechanical competence since the topology has been preserved. Accurate measurement of trabecular thickness is thus of paramount importance and an integral element of trabecular bone structure analysis.

The classical approach toward measuring trabecular thickness is based on histomorphometry of bone biopsies and involves measuring bone perimeter and area. Similarly, it is possible to obtain a measure of thickness in 2D images from a measurement of skeleton length and bone volume fraction, which has been shown to be feasible and providing precision adequate to quantify thickness even in images of relatively low resolution. It can readily be seen that the apparent thickness, Tb. Th, of an elongated structure in a cross-sectional image can be expressed as:

$$Tb.Th \approx BVF/(\Delta z \times L) \qquad \text{Equation 1}$$

where $\Delta z$ is the image slice thickness and L is the skeleton length. The equation is based on the assumption that $\Delta z$ is smaller than the thickness of trabeculae measured in the direction perpendicular to the image slice.

The limitation of these approaches is their 2D nature in that the measurement depends on the plane of the section relative to structural orientation. Hildebrand, et al., *J Microscopy*, 185:67-75, 1997 discloses a model-independent 3D method in which spheres are inscribed at points belonging to bone. At each point p thickness is defined as the radius of the largest inscribed sphere encompassing p. This approach is suited for high-resolution images that can easily be segmented, but is likely to fail when significant partial volume blurring is present. The latter is the case in images acquired the limited spatial resolution regime of in vivo micro-MRI.

The preferable method of measuring trabecular thickness uses a fuzzy distance transform (FDT), disclosed in a provisional application being filed concurrently herewith and incorporated herein by reference. This method effectively deals with the inherently fuzzy nature of images acquired at a voxel size comparable to, or greater than, the typical trabecular bone thickness. The distance transform of hard objects (e.g., binary structures) requires segmentation which may have is fraught with problems in the limited spatial resolution regime of in vivo MRI, where partial volume effects cause blurring of the trabecular boundaries. While in binary images the distance between two points is simply the length of the straight-line segment joining them, in a grayscale image of a fuzzy object the distance must be evaluated by considering all paths joining the two points. The length of a path $\pi$, $\Pi_s(\pi)$, in a fuzzy object, is defined as the integration of fuzzy membership values along $\pi$:

$$\Pi_s(\pi) = \int_0^1 \mu_s(\pi(t)) \left| \frac{d\pi(t)}{dt} \right| dt \qquad \text{Equation 2}$$

where the membership value $\mu_s(\pi(t))$ acts as a weighting factor and the derivative, $d\pi(t)/dt$ represents speed. This approach underlies the rationale that pixels representing reduced BVF (due to partial volume averaging) should be assigned commensurately reduced weight. The fuzzy distance between two points is then computed as the minimum length of all paths between the two points.

It is noted that FDT is an operator applied to a fuzzy subset that assigns a value at each location that is the smallest fuzzy distance between the location and the complement of the support of the fuzzy subset. In other words, FDT maps the "depth" at each point within the support of an object. FDT-based thickness computation, therefore, entails sampling these depth values along the medial axis of the target object.

Skeletonization is a widely used technique to generate a medial axis representation of an object. Therefore, the distribution of regional thickness over an object is calculated by sampling the FDT values along its skeleton. Although skeletonization could proceed directly from an object's fuzzy representation (i.e., BVF map), so far, a standard binary skeletonization has been used to obtain its medial axis representation. $Sk(\Theta(O))$ denote) the skeleton of $\Theta(O)$ with $\Theta(O)$ representing the support of object 0. The mean thickness of object O, $\tau(O)$, then is computed as the average of twice the FDT values along the skeleton $Sk(\Theta(O))$ as $$\tau(O) = \frac{\sum_{p \in Sk(\Theta(O))} 2\Omega_o(p)}{|Sk(\Theta(O))|} \qquad \text{Equation 3}$$

where $\Omega_0$ (p) is the minimum fuzzy distance from skeleton point p to the boundary. It suffices to mention that the dynamic programming algorithm that was implemented terminates in a finite number of steps and accurately computes digital FDT. The calculated thickness from Equation 3 is then corrected by subtracting an error correction therefrom. The error correction is calculated as:

$$\text{error} = -\frac{1}{\rho^3} \int \int_V \int \sqrt{(x^2 + y^2 + z^2)}\, dx\, dy\, dz \qquad \text{Equation 4}$$

where $\rho^3$ is the voxel size, and integration is over the entire voxel volume. Equation 4 assumes that all trabecular orientations are equally probable. In the case of highly anisotropic bone, such as in the case of the distal radius, where the trabeculae are predominantly oriented along the z direction, the third dimension can be ignored.

The method disclosed above is also robust with respect to noise. Addition of noise to images showed that above SNR~5 the error is on the order of 3-5%, but the algorithm returns significantly reduced thickness values at lower SNR, presumably since noise causes artificial cavities. The above disclosed methods of determining structural thickness are for exemplary purposes and should not be used to limit the present invention. As those skilled in the art know, other methods of determining structural thickness are known (e.g., tensor scale analysis and DTA-based numerical modeling) and can be used in accordance with the present invention.

In a preferred embodiment of the present invention, the information provided by the above network analysis is used to calculate a patient risk profile, indicating the patient's risk of a future fracture (Step 111). Alternatively, the parameters can be monitored in longitudinal studies as a means to evaluate the structural implications of disease progression or regression in response to treatment (Step 110). It is preferable to establish the patient profile using information utilized in and output from Step 109 that are sensitive to the network "quality" and disease etiology. Such etiology might result from the regional, as well as global analyses of the structural parameters, where the distribution of parameters within a particular anatomical site indicates the status of disease progression. This distribution has been seen, for example, in patients as a preferential loss of trabecular structure at the center of anatomical regions, such as the distal radius or proximal femur, where the biomechanical forces appear to be more diffuse than at the cortical contact points.

The evaluation of the patient, whether it is the treatment response or the patient profile, is reported to the patient and stored in a patient database for longitudinal monitoring or epidemiological studies (population statistics). (Step 112).

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A computerized system for analyzing trabecular bone structure of a selected anatomical region, the system comprising:

magnetic resonance imaging (MRI) coil for scanning or rescanning the trabecular bone in the immobilized selected region to generate MR bone image data, wherein image data comprises data acquired by signals emitted from bone marrow regions of the scanned trabecular bone;

computer processor(s) operably linked to the scanner, to produce processed or unprocessed image data or for creating derived quantitative parameters, or combinations thereof, permitting visualization or mapping of the derived parameters; operating computer readable medium comprising the data and parameters, and encoded with one of the following: computer program software; computer executable instructions or instructions executed by the computer processor;

computer code for processing the image data or for creating derived quantitative parameters, or combinations thereof, the code causing operations comprising, individually or in combination, a function for correcting the image data to compensate for movement of a selected region relative to the coil during the scanning; a function for deshading the image data to minimize the effects of radio frequency inhomogeneity; and a function for reducing noise in the image data, a function for determining trabecular thickness; a function for providing structural anisotropy; a function for providing topological analysis; and a function for calculating network strength;

and reporting component for outputting the processed image data or derived quantitative parameters, or for visualizing same, or combinations thereof.

2. The system of claim 1, comprising a mathematical function to calculate network strength of the scanned bone as a derived quantitative parameter.

3. The system of claim 1, comprising a function to provide topological analysis of the scanned bone as a derived quantitative parameter.

4. The system of claim 1, comprising a function to provide structural anisotropy of the scanned bone as a derived quantitative parameter.

5. The system of claim 1, comprising a function to determine trabecular thickness of the scanned bone as a derived quantitative parameter.

6. The system of claim 1, wherein the selected anatomical region comprises an artifact free portion of the scanned trabecular bone.

7. The system of claim 1, further comprising a process for determining the risk of bone fracture from output of the processed image data or derived quantitative parameters, or combinations thereof.

8. The system of claim 1, wherein the selected anatomical region comprising the scanned trabecular bone is in a patient.

9. An improved, scanned and processed image of trabecular bone structure produced by the system of claim 1.

10. A computerized system for analyzing trabecular bone structure of a selected anatomical region in a patient, the system comprising:

magnetic resonance imaging (MRI) coil for scanning or rescanning the trabecular bone in the immobilized selected region to generate MR bone image data, wherein image data comprises data acquired by signals emitted from bone marrow regions of the scanned trabecular bone;

computer processor(s) operably linked to the scanner, to produce processed or unprocessed image data or for creating derived quantitative parameters, or combinations thereof, permitting visualization or mapping of the derived parameters; operating computer readable medium comprising the data and parameters, and encoded with one of the following: computer program software; computer executable instructions or instructions executed by the computer processor;

computer code for processing the image data or for creating derived quantitative parameters, or combinations thereof, the code causing operations comprising, individually or in combination, a function for correcting the image data to compensate for movement of the patient relative to the coil during the scanning; a function for deshading the image data to minimize the effects of radio frequency inhomogeneity; and a function for reducing noise in the image data;

a function for determining trabecular thickness, a function for providing structural anisotropy; a function for providing topological analysis; and a function for calculating network strength;

and reporting component for outputting the processed image data or derived quantitative parameters, or for visualizing same, or combinations thereof.

11. The system of claim 10, comprising a mathematical function to calculate network strength of the scanned bone of the patient as a derived quantitative parameter.

12. The system of claim 10, comprising a function to provide topological analysis of the scanned bone of the patient as a derived quantitative parameter.

13. The system of claim 10, comprising a function to provide structural anisotropy of the scanned bone of the patient as a derived quantitative parameter.

14. The system of claim 10, comprising a function to determine trabecular thickness of the scanned bone of the patient as a derived quantitative parameter.

15. The system of claim 10, wherein the selected anatomical region comprises an artifact free portion of the scanned trabecular bone of the patient.

16. The system of claim 10, further comprising a process for determining the patient's risk of bone fracture from output of the processed image data or derived quantitative parameters, or combinations thereof.

17. An improved, scanned and processed image of trabecular bone structure of a patient produced by the system of claim 10.

* * * * *